(12) United States Patent
Kanzawa et al.

(10) Patent No.: US 6,737,379 B1
(45) Date of Patent: May 18, 2004

(54) ALUMINUM-OXY COMPOUND, CATALYST COMPONENT FOR POLYMERIZING OLEFIN, AND METHOD FOR PRODUCING POLYOLEFIN

(75) Inventors: Mitsugu Kanzawa, Ichihara (JP); Shuji Machida, Ichihara (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/601,332

(22) PCT Filed: Dec. 8, 1999

(86) PCT No.: PCT/JP99/06871

§ 371 (c)(1),
(2), (4) Date: Aug. 10, 2000

(87) PCT Pub. No.: WO00/34290

PCT Pub. Date: Jun. 15, 2000

(30) Foreign Application Priority Data

Dec. 10, 1998 (JP) ............................................. 10-351194

(51) Int. Cl.$^7$ ................................................. B01J 31/00
(52) U.S. Cl. ....................... 502/117; 526/127; 526/129; 526/135; 526/141; 526/160; 556/179; 556/187; 556/190

(58) Field of Search .......................... 502/117; 526/127, 526/129, 135, 141, 160; 556/179, 187, 190

(56) References Cited

U.S. PATENT DOCUMENTS 5,084,585 A * 1/1992 Maezawa et al. ............ 556/179
6,294,495 B1 * 9/2001 Matsunaga .................. 502/103

FOREIGN PATENT DOCUMENTS

| EP | 0 322 663 | 7/1989 |
| EP | 0 383 255 | 8/1990 |
| JP | 7-074410 | 3/1991 |

* cited by examiner

Primary Examiner—William Cheung
(74) Attorney, Agent, or Firm—Oblon, Spivak, McClelland, Maier & Neustadt, P.C.

(57) ABSTRACT

Provided are an aluminium-oxy compound obtained through reaction of an organoaluminium compound with water, which is soluble in hydrocarbon solvents and in which the amount of the organoaluminium compound remaining is at most 10% by weight; a carrier comprising the aluminium-oxy compound and an inorganic compound; and a catalyst component for olefin polymerization comprising the carrier and a transition metal compound. The catalyst component for olefin polymer production comprises the aluminium-oxy compound and gives polyolefins with good polymer morphology.

16 Claims, No Drawings

ALUMINUM-OXY COMPOUND, CATALYST COMPONENT FOR POLYMERIZING OLEFIN, AND METHOD FOR PRODUCING POLYOLEFIN

TECHNICAL FIELD

The present invention relates to a novel aluminum-oxy compound, a carrier for olefin polymerization catalyst comprising the aluminum-oxy compound, a catalyst component for olefin polymerization, and a method for producing polyolefins. More precisely, it relates to a novel aluminum-oxy compound having high polymerization activity and capable of giving polyolefins with good polymer morphology, a carrier for olefin polymerization catalysts comprising the aluminum-oxy compound, a catalyst component for olefin polymerization, and a method for producing polyolefins.

BACKGROUND OF THE INVENTION

In the field of polyolefin production, forwarded is the development of catalyst systems applicable to bulk polymerization, vapor-phase polymerization, slurry polymerization and others, for catalysts with transition metal compounds, typically IV Group transition metal compounds carried on inorganic porous carriers (these will be hereinafter referred to as transition metal-carrying catalysts).

The polymerization systems require high polymerization activity and good polymer morphology, for which is desired the development of high-activity catalysts capable of giving high bulk-density polyolefins.

On the other hand, it is known that aluminum-oxy compounds, especially methylalumoxane are useful promoters for metallocene catalysts. For example, various techniques of producing on-carrier catalysts have been disclosed, for example, using a solution of methylalumoxane in the step of carrying transition metal compounds on inorganic porous carriers. However, it is known that aluminum-oxy compounds produced from organoaluminums often contain impurities of non-reacted organoaluminiums and insoluble side products (gels). Therefore, the polymerization activity per aluminum atom of aluminum-oxy compounds is low, and a large amount of the compound must be used for polymerization, thereby inevitably resulting in the increase in the production costs. In addition, a large amount of aluminum will remain in the polymers produced. Such problems with aluminum-oxy compounds are serious for their industrial applications. To solve the problems, various proposals have heretofore been made (Japanese Patent Application Laid-Open Nos. 211307/1986, 130601/1988, 16803/1989, 167307/1990).

According to the techniques proposed, the activity per aluminum compound of aluminum-oxy compounds could be increased in some degree, but such aluminoxanes are still problematic in that they are poorly soluble and are difficult to handle, and, in addition, they often worsen the quality and even the tone of the polymers produced. Therefore, further improving the compounds is desired.

Also proposed is a method of combining methylaluminoxane and some other organoaluminum compounds (Japanese Patent Laid-Open Nos. 260602/1985, 130604/1985, 89506/1988, 178108/1988, 218707/1988, 9206/1989, 315407/1989, 22306/1990, 167310/1990).

According to the techniques proposed, the amount of methylaluminoxane to be used could be reduced in some degree, but the activity per aluminum of the combined systems is still unsatisfactory. Therefore, further improving them is desired.

Apart from the problems with aluminum-oxy compounds themselves noted above, there is still another problem with transition metal-carrying catalyst systems comprising a transition metal, an inorganic porous carrier and an aluminum-oxy compound in that their catalytic activity is much lower than that of non-carrier homogeneous-phase catalyst systems. To solve this problem, various proposals have been made.

For example, International Patent Publication No. 507515/1997 discloses a method of preparing an on-carrier catalyst, for which the alumoxane solution to be used is pre-treated to remove the gel component from it. The object of the technique disclosed is to improve polymer morphology, but, according to the method, it is difficult to increase the activity of the catalyst. In addition, the technique to improve polymer morphology is limited.

International Patent Publication Nos. 511044/1996, 503008/1997, 505340/1997 and 507517/1997 disclose various methods of using alumoxane solutions for producing on-carrier catalysts. However, the on-carrier catalysts produced according to the methods are problematic in that their catalytic activity is much lower than that of non-carrier homogeneous-phase catalysts.

U.S. Pat. No. 5,157,137 discloses a method of processing an alumoxane solution with alkali to remove the gel component from it. However, the technique disclosed is ineffective for increasing the activity of catalysts, and, in addition, the alkali treatment is problematic in that it increases the cost of alumoxanes.

As mentioned above, the current situation in the art regarding transition metal-carrying catalyst systems that comprise a transition metal compound, an inorganic porous carrier and an aluminium-oxy compound is that no one could obtain on-carrier catalysts of which the polymerization activity is on the same level as that of non-carrier homogeneous-phase catalysts and which could give high bulk-density polyolefins.

We, the present inventors have made the present invention from the viewpoints noted above, and the object of the invention is to provide a novel aluminum-oxy compound having high polymerization activity and capable of giving polyolefins with good polymer morphology, a carrier for olefin polymerization catalysts comprising the aluminum-oxy compound, a catalyst component for olefin polymerization, and a method for producing polyolefins.

We, the present inventors have assiduously studied, and, as a result, have found a specific aluminum-oxy compound which is obtained from a reaction product of an organoaluminum compound and water and which contains neither a residual organoaluminum component nor a gel compound; a carrier for olefin polymerization catalysts which is obtained from the aluminum-oxy compound and an inorganic compound; and an olefin polymerization catalyst which is obtained by contacting the carrier with a transition metal compound. We have further found that the olefin polymerization catalyst has high polymerization activity and that polyolefins with good polymer morphology can be obtained by the use of the catalyst. On the basis of these findings, we have completed the present invention.

Specifically, the invention provides an aluminum-oxy compound, a carrier for olefin polymerization catalysts, a catalyst component for olefin polymerization, and a method for producing polyolefins, which are as follows:

1. An aluminium-oxy compound obtained through reaction of an organoaluminum compound with water, which is soluble in hydrocarbon solvents and in which the amount of the organoaluminum compound remaining is at most 10% by weight as measured through $^1$H-NMR.
2. A carrier for olefin polymerization catalysts, which comprises the aluminum-oxy compound of above 1 and an inorganic compound having at least one element selected from Groups 2 to 4 or Groups 12 to 14 of the Periodic Table.
3. The carrier for olefin polymerization catalysts of above 2, wherein the inorganic compound is an oxide.
4. A catalyst component for olefin polymerization, which comprises the carrier for olefin polymerization catalysts of above 2 or 3 and a transition metal compound.
5. The catalyst component for olefin polymerization of above 4, wherein the transition metal compound is selected from Group 4 or Groups 8 to 10 of the Periodic Table.
6. The catalyst component for olefin polymerization of above 4 or 5, wherein the transition metal compound of Group 4 of the Periodic Table is any one selected from transition metal compounds of the following general formulae (I) to (III):

(I)

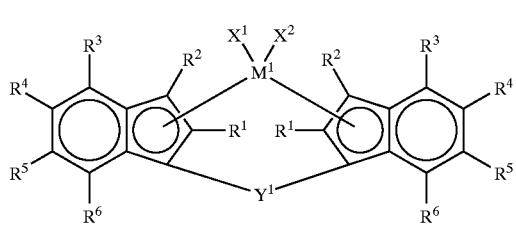

where $R^1$ to $R^6$ each independently represent a hydrogen atom, a halogen atom, a hydrocarbon group having from 1 to 20 carbon atoms, or a halogen-containing hydrocarbon, group having from 1 to 20 carbon atoms; the groups of at least one pair of $R^3$ and $R^4$, $R^4$ and $R^5$, and $R^5$ and $R^6$ may be bonded to each other to form a ring; $X^1$ and $X^2$ each independently represent a hydrogen atom, a halogen atom, or a hydrocarbon group having from 1 to 20 carbon atoms; $Y^1$ is a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, —SO$_2$—, —NR$^7$—, —PR$^7$—, —P(O)R$^7$—, —BR$^7$— or —AlR$^7$—; $R^7$ represents a hydrogen atom, a halogen atom, a hydrocarbon group having from 1 to 20 carbon atoms, or a halogen-containing hydrocarbon group having from 1 to 20 carbon atoms; $M^1$ represents titanium, zirconium or hafnium;

(II)

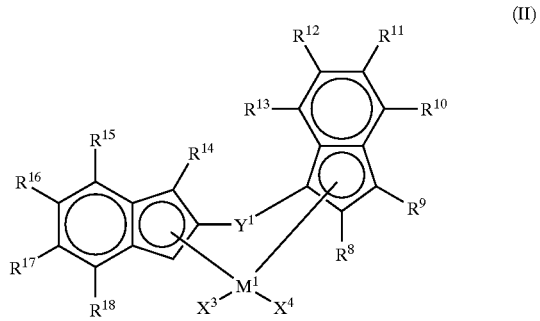

where $R^8$ to $R^{18}$, $X^3$ and $X^4$ each independently represent a hydrogen atom, a halogen atom, a hydrocarbon group having from 1 to 20 carbon atoms, a halogen-containing hydrocarbon group having from 1 to 20 carbon atoms, a silicon-containing group, an oxygen-containing group, a sulfur-containing group, a nitrogen-containing group, or a phosphorus-containing group; $R^{10}$ and $R^{11}$, as well as $R^{15}$ and $R^{16}$ may be bonded to each other to form a ring; $X^3$ and $X^4$ each independently represent a halogen atom, a hydrocarbon group having from 1 to 20 carbon atoms, a halogen-containing hydrocarbon group having from 1 to 20 carbon atoms, a silicon-containing group, an oxygen-containing group, a sulfur-containing group, a nitrogen-containing group, or a phosphorus-containing group; $Y^1$ is a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, —SO$_2$—, —NR$^7$—, —PR$^7$—, —P(O)R$^7$—, —BR$^7$— or —AlR$^7$—; $R^7$ represents a hydrogen atom, a halogen atom, a hydrocarbon group having from 1 to 20 carbon atoms, or a halogen-containing hydrocarbon group having from 1 to 20 carbon atoms; $M^1$ represents titanium, zirconium or hafnium;

(III)

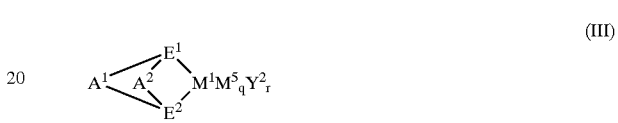

where $M^1$ represents titanium, zirconium or hafnium; $E^1$ and $E^2$ each represent a ligand selected from a cyclopentadienyl group, a substituted cyclopentadienyl group, an indenyl group, a substituted indenyl group, a heterocyclopentadienyl group, a substituted heterocyclopentadienyl group, an amido group, a phosphido group, a hydrocarbon group and a silicon-containing group, and they form a crosslinked structure via $A^1$ and $A^2$, and they may be the same or different; $X^5$ represents a σ-bonding ligand, and plural $X^5$'s, if any, may be the same or different, and may be crosslinked with any of other $X^5$, $E^1$, $E^2$ or $Y^2$; $Y^2$ represents a Lewis base, and plural $Y^2$'s, if any, may be the same or different, and may be crosslinked with any of other $Y^2$, $E^1$, $E^2$ or $X^5$; $A^1$ and $A^2$ each are a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, —SO$_2$—, —NR$^7$—, —PR$^7$—, —P(O)R$^7$—, —BR$^7$— or —AlR$^7$—, and they may be the same or different; $R^7$ represents a hydrogen atom, a halogen atom, a hydrocarbon group having from 1 to 20 carbon atoms, or a halogen-containing hydrocarbon group having from 1 to 20 carbon atoms; q represents an integer of from 1 to 5, equaling to [(atomic valency of $M^1$)–2]; and r represents an integer of Li from 0 to 3.
7. The catalyst component for olefin polymerization of above 5, wherein the transition metal compound of Groups 8 to 10 of the Periodic Table has a diimine compound as the ligand.
8. A catalyst component for olefin polymerization, which comprises the catalyst g,J component for olefin polymerization of any one of above 5 to 7 and an organoaluminum compound.
9. A method for producing polyolefins, which comprises polymerizing olefins in the presence of the catalyst component for olefin polymerization of any one of above 4 to 8.

BEST MODES OF CARRYING OUT THE INTENTION

The invention is described in detail hereinunder.
[1] Aluminum-oxy compound:
The aluminum-oxy compound of the invention is obtained through reaction of an organoaluminum compound with water.

This is soluble in hydrocarbon solvents, and the amount of the organoaluminum compound remaining in this is at most 10% by weight as measured through $^1$H-NMR. In the invention, the ratio of the inorganic compound to be carried on the aluminum-oxy compound (this will be hereinafter referred to as on-carrier ratio) increases. Therefore, it is desirable that the amount of the organoaluminum remaining in the aluminum-oxy compound falls between 3 and 5% by weight, more preferably between 2 and 4% by weight. If the amount of the remaining organoaluminum compound is larger than 10% by weight, such is unfavorable, since the on-carrier ratio will lower and therefore the polymerization activity of the catalyst Twill lower. The aluminum-oxy compound of the invention is soluble in hydrocarbon solvents. Therefore, one advantage of the invention is that the aluminum-oxy compound not carrying an inorganic compound thereon could be recycled. In addition, the aluminum-oxy compound has stable properties. Therefore, another advantage of the invention is that the aluminum-oxy compound does not require any specific treatment before its use. If the aluminum-oxy compound contains some impurities not soluble in hydrocarbon solvents, such is unfavorable, since the insoluble impurities will have some negative influences on the mean grain size and the grain size distribution (these are known generally as morphology) of polyolefins produced. The method of obtaining the aluminum-oxy compound having a remaining organoaluminum content of not larger than 10% by weight is not specifically defined. For example, employable is a method of heating a solution of an aluminum-oxy compound under reduced pressure to completely remove the solvent through evaporation to give a dry solid (this may be referred to as a dry-up method).

In the dry-up method, preferably, the solvent is evaporated away under heat up to 80° C., more preferably up to 60° C., under reduced pressure. If the aluminum-oxy solution is heated above 80° C., the insoluble component will greatly increase therein, and the activity of the transition metal-carrying catalyst comprising the aluminum-oxy compound produced at such high temperatures will be low. The degree of reduced pressure for the method may be generally 30 mmHg or lower, but preferably 20 mmHg or lower.

The organoaluminum content may be determined generally according to the method described in Organometallics, Vol. 17, No. 10, 1998, pp. 1941–1945.

The aluminum-oxy compound of the invention is characterized in that it is soluble in hydrocarbon solvents. Conventional aluminum-oxy compounds generally contain some substances not soluble in hydrocarbon solvents, but the aluminum-oxy compound of the invention dose not contain such substances not soluble in hydrocarbon solvents. Accordingly, the advantage of the aluminum-oxy compound of the invention as a catalyst for olefin polymerization is that the fine powder content of the polymer produced is small and the grains of the polymer have a large mean grain size, or that is, the polymer has good morphology.

The hydrocarbon solvents include aromatic hydrocarbons such as benzene, toluene, xylene, cumeme, cymene, etc.; aliphatic hydrocarbons such as pentane, hexane, heptane, octane, decane, dodecane, hexadecane, octadecane, etc.; alicyclic hydrocarbons such as cyclopentane, cyclohexane, cyclooctane, methylcyclopentane, etc.; petroleum fractions such as naphtha, kerosene, light gas oil, etc. Of those, preferred are aromatic hydrocarbons.

The method of removing the substances insoluble in hydrocarbon solvent such as those mentioned above, from the aluminum-oxy compound is not specifically defined. For example, employable is a method of spontaneously depositing the hydrocarbon-insoluble substances in a hydrocarbon solvent followed by removing the deposit through decantation. Apart from this, also employable is a method of removing the insoluble substances through centrifugation or the like. After this, it is desirable that the recovered, soluble component is filtered through a G5 glass filter or the like in a nitrogen stream atmosphere, whereby the insoluble substances could be removed more completely. The aluminum-oxy compound thus produced in the manner as above will gel, while stored, to have an increased gel component. Therefore, it is desirable that the aluminum-oxy compound is used within a period of 48 hours after its preparation, more preferably immediately after its preparation. The ratio of the aluminum-oxy compound of the invention to the hydrocarbon solvent is not specifically defined, but is preferably such that the concentration of the aluminum atom in the aluminum-oxy compound is from 0.5 to 10 mols relative to one liter of the hydrocarbon solvent.

The aluminum-oxy compound of the invention is not specifically defined, provided that it is obtained through reaction of an organoaluminum compound with water, and includes various types of aluminum-oxy compounds. For example, it includes commercial products from Albemarle Corporation, those from Ethyl Corporation, those from Shering Corporation, etc.

In addition, it includes aluminum-oxy compounds of so-called linear aluminoxanes of the following general formula (IV) as well as cyclic aluminoxanes of the following general formula (V). The basic skeletons of those compounds are described in many known references.

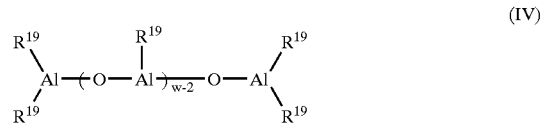

(IV)

wherein $R^{19}$ represents a hydrocarbon group, such as an alkyl, alkenyl, aryl or arylalkyl group having from 1 to 20, but preferably from 1 to 12 carbon atoms, or represents a halogen atom; w indicates a mean degree of polymerization of the compound and is generally an integer of from 2 to 50, but preferably from 2 to 40; and plural $R^{19}$'s may be the same or different.

(V)

wherein $R^{19}$ and w have the same meanings as in formula (IV).

For producing those aluminoxanes, for example, an organoaluminum compound may be contacted with a condensing agent such as water or the like. However, the method for producing them is not specifically defined. The aluminoxanes could be produced in any known manner. For example, (1) an organoaluminum compound is dissolved in an organic solvent, and then contacted with water; (2) an organoaluminum is previously added to the polymerization system that requires the aluminoxane, and water is added to the system in later stages; (3) crystal water existing in metal salts and others, or water having adsorbed to inorganic or organic materials is reacted with an organoaluminum compound; or (4) a tetraalkyldialuminoxane is reacted with a trialkylaluminum and then with water. The aluminoxane may be insoluble in toluene.

Any others produced in known techniques disclosed in known references are also usable herein. The known reference include, for example, Japanese Patent Laid-Open Nos. 328520/1997, 278824/1997, etc. In the invention, one or more of those aluminoxanes may be used either singly or as combined.

The organoaluminum compound to be the starting material for the aluminum-oxy compound of the invention is not specifically defined, and includes various types of organoaluminum compounds. For example, usable are alkyl group-having aluminum compounds of a general formula (VI):

$$R^{20}{}_mAl(OR^{21})_nX_{3-m-n} \quad (VI)$$

wherein $R^{20}$ and $R^{21}$ each represent an alkyl group having from 1 to 8, preferably from 1 to 4 carbon atoms; X represents a hydrogen atom or a halogen atom; $0<m\leq 3$, preferably m=2 or 3, most preferably m=3; $0\leq n<3$, preferably n=0 or 1.

Concretely, they include trialkylaluminum compounds such as trimethylaluminum, triethylaluminum, tripropylaluminum, triisopropylaluminum, tri-n-butylaluminum, triisobutylaluminum, tri-sec-butylmethylaluminum, tri-tert-butylmethylaluminum, tripentylaluminum, trihexylaluminum, trioctylaluminum, tridecylaluminum, tricyclohexylatuminum, tricyclooctylaluminum, etc.; halogen-, alkoxy group- or hydroxyl group-having alkylaluminum compounds such as dimethylaluminum chloride, diethylaluminum chloride, ethylaluminum sesquichloride, dimethylaluminum methoxide, diethylaluminum methoxide, dimethylaluminum hydroxide, diethylaluminum hydroxide, etc.; hydrogen atom-having aluminum compounds such as dimethylaluminum hydride, diisobutylaluminum hydride, etc. In the invention, one or more of those organoaluminum compounds may be used either singly or as combined.

[2] Carrier for olefin polymerization catalysts:

The carrier for olefin polymerization catalysts of the invention is obtained by contacting the aluminum-oxy compound with an inorganic compound containing at least one element selected from Groups 2 to 4 and Groups 12 to 14 of the Periodic Table. The inorganic compound is preferably an inorganic oxide, as increasing the on-carrier ratio of the aluminum-oxy compound. More preferably, the inorganic oxide is in the form of porous fine grains, as further increasing the on-carrier ratio. In the carrier for olefin polymerization catalysts of the invention, the on-carrier ratio of the aluminum-oxy compound may fall between 30 and 90%, preferably between 40 and 90%, more preferably between 50 and 90%, even more preferably between 60 and 90%, still more preferably between 70 and 90%, in terms of the ratio of grams of the aluminum-oxy compound to one gram of the inorganic compound. The on-carrier ratio is preferably higher, as the amount of the inorganic compound to be used in olefin polymerization could be smaller and therefore the production costs could be reduced. In addition, the higher on-carrier ratio has another advantage of polymer quality improvement, as the impurities to remain in the polymer produced could be reduced.

At least one element selected from Groups 2 to 4 and Groups 12 to 14 of the Periodic Table includes C, Mg, Al, Si, Ca, Sc, Ti, B, Tl, Ge, Sn, Zn, Ba, Pb, Y, Sr, Th, etc. Concretely, the inorganic compound includes $SiO_2$, $Al_2O_3$, MgO, $ZrO_2$, $TiO_2$, $Fe_2O_3$, $B_2O_3$, CaO, ZnO, BaO, $ThO_2$, and their mixtures, such as silica-alumina, zeolite, ferrite, glass fibers, etc. The inorganic oxide may contain a small amount of carbonates, nitrates, sulfates, etc.

Other examples of the inorganic compounds than those mentioned above include magnesium compounds of a general formula, $MgR^{22}{}_xX^6{}_y$, such as typically $MgCl_2$, $Mg(OC_2H_5)_2$, and also their complexes. In the formula, $R^{22}$ represents an alkyl group having from 1 to 20 carbon atoms, an alkoxy group having from 1 to 20 carbon atoms, or an aryl group having from 6 to 20 carbon atoms; $X^6$ represents a halogen atom, or an alkyl group having from 1 to 20 carbon atoms; x falls between 0 and 2, y falls between 0 and 2, and x+y=2; plural $R^{22}$'s as well as plural $X^6$'s, if any, may be the same or different.

The inorganic compound for use in the invention is preferably $MgCl_2$, $MgCl(OC_2H_5)$, $Mg(OC_2H_5)_2$, $SiO_2$, $Al_2O_3$, etc. Of those, especially preferred are $SiO_2$ and $Al_2O_3$. The properties of the inorganic compound vary, depending on the type of the compound and also on the method of producing it. In general, the compound is granular, having a mean grain size of from 1 to 300 $\mu$m preferably from 10 to 200 $\mu$m, more preferably from 20 to 100 $\mu$m.

It the grain size of the compound is too small, fine powder will increase in the polymer produced; but if too large, coarse grains will increase in the polymer whereby the bulk density of the polymer will be lowered and the polymer will clog hoppers.

The specific surface area of the inorganic compound generally falls between 1 and 1000 $m^2/g$, but preferably between 50 and 500 $m^2/g$; and the pore volume thereof generally falls between 0.1 and 5 $cm^3/g$, but preferably between 0.3 and 3 $cm^3/g$.

If any of the specific surface area and the pore volume of the compound oversteps the defined range, the catalyst activity will be poor. The specific surface area and the pore volume can be obtained, for example, from the volume of nitrogen gas absorption to be measured according to the BET method (see J. Am. Chem. Soc., Vol. 60, p. 309, 1983).

More desirably, the inorganic compound is baked generally at a temperature falling between 150 and 1000° C., but preferably between 200 and 800° C.

The carrier for olefin polymerization catalysts of the invention can be produced by contacting the aluminium-oxy compound with the inorganic compound. In general, contacting the two maybe effected in the solvent mentioned above, in which the concentration of the compounds may fall between 0.1 and 10.0 mols/liter. The temperature may be 20° C. or lower, and the time maybe 0.5 hours or longer. Preferably, the concentration falls between 0.5 and 5.0 mols/liter, the temperature is not higher than 0° C., and the time is not shorter than 1.0 hour.

[3] Catalyst Component for Olefin Polymerization:

D The catalyst component for olefin polymerization of the invention is prepared by contacting the carrier for olefin polymerization catalysts mentioned above, with a transition metal compound.

The transition metal compound for use in the invention is not specifically defined, and any and every transition metal compound capable of being formed into catalysts for polyolefin production is employable herein. Above all, preferred are transition metal compounds of Group 4 of the Periodic Table and transition metal compounds of Groups 8 to 10 thereof.

The transition metal compounds of Group 4 of the Periodic Table are not specifically defined. They include, for example, (a) transition metal catalyst components for Ziegler-Natta catalysts that comprise a transition compound with any of titanium, zirconium or hafnium, and an organometallic compound; (b) transition metal catalyst components for high-activity on-carrier catalysts that comprise a combination of any of a transition metal compound, an organoaluminum compound and an electron donor as carried on a carrier such as magnesium chloride or the like; and (c) transition metal catalyst components for metallocene catalysts that comprise a combination of an aluminoxane and a transition metal compound having a cyclopentadienyl skeleton, an indenyl skeleton or the like as the ligand moiety. In (a), the transition metal compound may be a transition metal halide, including, for example, titanium trichloride, titanium tetrachloride, etc. The organometallic compound may be an organoaluminum compound, including, for example, trialkylaluminums, alkylaluminum halides, etc. In (b), the transition metal compound may also be a transition metal halide such as that mentioned above. The carrier may be a magnesium compound, and preferred are magnesium halides, etc. The electron donor includes, for example, esters, ethers, etc. Specific examples of the compounds are described in Japanese Patent Publication Nos. 19334/1983, 41676/1972, 16167/1981, 52166/1984, 38285/1991, 75245/1992, etc . In (c), the transition metal compound includes the compounds described in International Patent Publication No. 511044/1996, and Japanese Patent Laid-Open Nos. 100597/1994, 25350/1994, 184179/1994, 345809/1989, 19309/1983, 19306/1983, 19307/1983, 19308/1983, 130314/1986, 142005/1988, 268308/1992, 306304/1993, 100579/1994, 157661/1994, 149815/1995, 188318/1995, 258321/1995, etc.

Above all, transition metal compounds having a cyclopentyl and indenyl skeleton are preferred for use in the invention. Concretely, preferred are transition metal compounds selected fromthoseof the followinggeneral formulae (I) to (III).

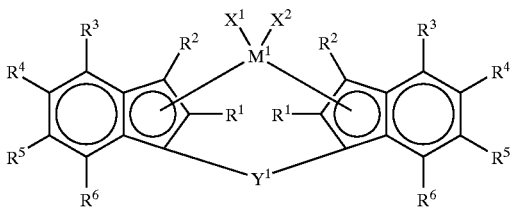

(I)

wherein $R^1$ to $R^6$ each independently represent a hydrogen atom, a halogen atom, a hydrocarbon group having from 1 to 20 carbon atoms, or a halogen-containing hydrocarbon group having from 1 to 20 carbon atoms; the groups of at least one pair of $R^3$ and $R^4$, $R^4$ and $R^5$, and $R^5$ and $R^6$ may be bonded to each other to form a ring; $X^1$ and $X^2$ each independently represent a hydrogen atom, a halogen atom, or a hydrocarbon group having from 1 to 20 carbon atoms; $Y^1$ is a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, —SO$_2$—, —NR$^7$—, —PR$^7$—, —P(O)R$^7$—, —BR$^7$— or —AlR$^7$—; $R^7$ represents a hydrogen atom, a halogen atom, a hydrocarbon group having from 1 to 20 carbon atoms, or a halogen-containing hydrocarbon group having from 1 to 20 carbon atoms; $M^1$ represents titanium, zirconium or hafnium.

The transition metal compounds of formula (I) where the groups of at least one pair of $R^3$ and $R^4$, $R^4$ and $R^5$, and $R^5$ and $R^6$ are bonded to each other to form a ring are compounds well known as BASF-type complexes.

In formula (I), the halogen atom for $R^1$ to $R^6$ includes chlorine, bromine, fluorine and iodine atoms. The hydrocarbon group having from 1 to 20 carbon atoms includes, for example, an alkyl group such as a methyl group, an ethyl group, an n-propyl group, an isopropyl group, an n-butyl group, an isobutyl group, a tert-butyl group, an n-hexyl group, an n-decyl group, etc.; an aryl group such as a phenyl group, a 1-naphthyl group, a 2-naphthyl group, etc.; an aralkyl group such as a benzyl group, etc. The halogen-containing hydrocarbon group having from 1 to 20 carbon atoms may be derived from the hydrocarbon group as above by substituting at least one hydrogen atom therein with a suitable halogen atom. These $R^1$ to $R^6$ may be the same or different. Of those, the neighboring groups of at least one pair of $R^3$ and $R^4$, $R^4$ and $R^5$, and $R^5$ and $R^6$ shall be bonded to each other to form a ring. The indenyl group having such a cyclic structure includes, for example, a 4,5-benzoindenyl group, an α-acenaphthoindenyl group, and their C1–10 alkyl-substituted derivatives.

The halogen atom for $X^1$ and $X^2$ includes chlorine, bromine, fluorine and iodine atoms. The hydrocarbon group having from 1 to 20 carbon atoms includes, for example, an alkyl group such as a methyl group, an ethyl group, a propyl group, an isopropyl group, an n-butyl group, a tert-butyl group, an n-hexyl group, etc.; an aryl group such as a phenyl group, etc.; an aralkyl group such as a benzyl group, etc. $X^1$ and $x^2$ may be the same or different. $Y^1$ is a divalent crosslinking group via which the two ligands are bonded to each other. The divalent hydrocarbon group having from 1 to 20 atoms for it includes, for example, an alkylene group such as a methylene group, a dimethylmethylene group, a 1,2-ethylene group, a dimethyl-1,2-ethylene group, a 1,4-tetramethylene group, a 1,2-cyclopropylene group, etc.; an arylalkylene group such as a diphenylmethylene group, etc. The divalent, halogen-containing hydrocarbon group having from 1 to 20 carbon atoms includes, for example, a chloroethylene group, a chloromethylene group, etc. The divalent silicon-containing group includes, for example, a methylsilylene group, a dimethylsilylene group, diethylsilylene group, a diphenylsilylene group, a methylphenylsilylene group, etc. The germanium-containing group and the tin-containing group include, for example, those of the silicon-containing group noted above where the silicon atom is replaced with germanium or tin. In general, the two ligands bonded to each other via $Y^1$ are the same, but may differ as the case may be.

The transition metal compounds of formula (I) are described, for example, in Japanese Patent Laid-Open Nos. 184179/1994, 345809/1994, etc. Specific examples of the compounds are benzoindenyl or acenaphtoindenyl compounds such as rac-dimethylsilanediyl-bis-1-(2-methyl-4,5-benzoindenyl)zirconium dichloride, rac-phenyliethylsilanediyl-bis-1-(2-methyl-4,5-benzoindenyl) zirconium dichloride, rac-ethanediyl-bis-1-(2-methyl-4,5-benzoindenyl)zirconium dichloride, rac-butanediyl-bis-1-(2-methyl-4,5-benzoindenyl)zirconium dichloride, rac-dimethylsilanediyl-bis-1-(4,5-benzoindenyl)zirconium dichloride, rac-dimethylsilanediyl-bis-1-(2-methyl-α-methyl-α-acenaphthoindenyl)zirconium dichloride, rac-phenylmethylsilanediyl-bis-1-(2-methyl-α-acenaphthoindenyl)zirconium dichloride, etc.; and those derived from them by substituting zirconium therein with titanium or hafnium.

In the indenyl skeleton of the transition metal compounds of formula (I), none of the pairs of $R^3$ and $R^4$, $R^4$ and $R^5$, and $R^5$ and $R^6$ may form a ring. The transition metal compounds having an indenyl skeleton of that type, and even others corresponding to those and having a 4,5,6,7-tetrahydroindenyl skeleton are also usable herein. These transition metal compounds are known as Hoechst complexes. They are described, for example, in Japanese Patent Laid-Open Nos. 268308/1992, 306304/1993, 100579/1994, 157661/1994, 149815/1995, 188318/1995, 258321/1995, etc.

Specific examples of the compounds are aryl-substituted compounds such as dimethylsilanediyl-bis-1-(2-methyl-4-phenylindenyl)zirconium dichloride, dimethylsilanediyl-bis-1-[2-methyl-4-(1-naphthyl)indenyl]zirconium dichloride, dimethylsilanediyl-bis-1-(2-ethyl-4-phenylindenyl)zirconium dichloride, dimethylsilanediyl-bis-1-[2-ethyl-4-(1-naphthyl)indenyl]zirconium dichloride, phenylmethylsilanediyl-bis-1-(2-methyl-4-phenylindenyl)zirconium dichloride, phenylmethylsilanediyl-bis-1-[2-methyl-4-(1-naphthyl)indenyl]zirconium dichloride, phenylmethylsilanediyl-bis-1-(2-ethyl-4-phenylindenyl)zirconium dichloride, phenylmethylsilanediyl-bis-1-[2-ethyl-4-(1-naphthyl)indenyl]zirconium dichloride, etc.; 2,4-substituted compounds such as rac-dimethylsilylene-bis-1-(2-methyl-4-ethylindenyl)zirconium dichloride, rac-dimethylsilylene-bis-1-(2-methyl-4-isopropylindenyl)zirconium dichloride, rac-dimethylsilylene-bis-(2-methyl-4-tert-butylindenyl)zirconium dichloride, rac-phenylmethylsilylene-bis-1-(2-methyl-4-isopropylindenyl)zirconium dichloride, rac-dimethylsilylene-bis-1-(2-ethyl-4-methylindenyl)zirconium dichloride, rac-dimethylsilylene-bis-1-(2,4-dimethylindenyl)zirconium dichloride, rac-dimethylsilylene-bis-1-(2-methyl-4-ethylindenyl)zirconiumdimethyl, etc.; 4,7-substituted, 2,4,7-substituted, or 3,4,7-substituted compounds such as rac-dimethylsilylene-bis-1-(4,7-dimethylindenyl)zirconium dichloride, rac-1,2-ethanediyl-bis-1-(2-methyl-4,7-dimethylindenyl)zirconium dichloride, rac-dimethylsilylene-bis-1-(3,4,7-trimethylindenyl)zirconium dichloride, rac-1,2-ethanediyl-bis-1-(4,7-dimethylindenyl)zirconium dichloride, rac-1,2-butanediyl-bis-1-(4,7-dimethylindenyl)zirconium dichloride, etc.; 2,4,6-substituted compounds such as dimethylsilanediyl-bis-1-(2-methyl-4,6-diisopropylindenyl)zirconium dichloride, phenylmethylsilanediyl-bis-1-(2-methyl-4,6-diisopropylindenyl)zirconium dichloride, rac-dimethylsilanediyl-bis-1-(2-methyl-4,6-diisopropylindenyl)zirconium dichloride, rac-1,2-ethanediyl-bis-1-(2-methyl-4,6-diisopropylindenyl)zirconium dichloride, rac-diphenylsilanediyl-bis-1-(2-methyl-4,6-diisopropylindenyl)zirconium dichloride, rac-phenylmethylsilanediyl-bis-1-(2-methyl-4,6-diisopropylindenyl)zirconium dichloride, rac-dimethylsilanediyl-bis-1-(2,4,6-trimethylindenyl)zirconium dichloride, etc.; 2,5,6-substituted compounds such as rac-dimethylsilanediyl-bis-1-(2,5,6-trimethylindenyl)zirconium dichloride, etc.; 4,5,6,7-tetrahydroindenyl compounds such as rac-dimethylsilylene-bis(2-methyl-4,5,6,7-tetrahydro-1-indenyl)zirconium dichloride, rac-ethylene-bis-(2-methyl-4,5,6,7-tetrahydro-1-indenyl)zirconium dichloride, rac-dimethylsilylene-bis(2-methyl-4,5,6,7-tetrahydro-1-indenyl)zirconiumdimethyl, rac-ethylene-bis(2-methyl-4,5,6,7-tetrahydro-1-indenyl)zirconiumdimethyl, rac-ethylene-bis(4,7-dimethyl-4,5,6,7-tetrahydro-1-indenyl)zirconium dichloride, etc.; and those derived from the zirconium compounds by substituting zirconium therein with titanium or hafnium, etc.

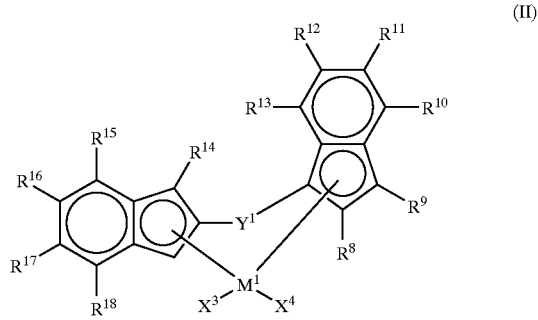

(II)

wherein $R^8$ to $R^{18}$, $X^3$ and $X^4$ each independently represent a hydrogen atom, a halogen atom, a hydrocarbon group having from 1 to 20 carbon atoms, a halogen-containing hydrocarbon group having from 1 to 20 carbon atoms, a silicon-containing group, an oxygen-containing group, a sulfur-containing group, a nitrogen-containing group, or a phosphorus-containing group; $R^{10}$ and $R^{11}$, as well as $R^{15}$ and $R^{16}$ may be bonded to each other to form a ring; $X^3$ and $X^4$ each independently represent a halogen atom, a hydrocarbon group having from 1 to 20 carbon atoms, a halogen-containing hydrocarbon group having from 1 to 20 carbon atoms, a silicon-containing group, an oxygen-containing group, a sulfur-containing group, a nitrogen-containing group, or a phosphorus-containing group; $Y^1$ is a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, —SO$_2$—, —NR$^7$—, —PR$^7$—, —P(O)R$^7$—, —BR$^7$— or —AlR$^7$—; $R^7$ represents a hydrogen atom, a halogen atom, a hydrocarbon group having from 1 to 20 carbon atoms, or a halogen-containing hydrocarbon group having from 1 to 20 carbon atoms; $M^1$ represents titanium, zirconium or hafnium.

The compounds of formula (II) are single-crosslinked complexes.

In formula (II), the halogen atom for $R^8$ to $R^{18}$, and $X^3$ and $X^4$ includes chlorine, bromine, fluorine and iodine atoms. The hydrocarbon group having from 1 to 20 carbon atoms includes, for example, an alkyl group such as a methyl group, an ethyl group, an n-propyl group, an isopropyl group, an n-butyl group, an isobutyl group, a tert-butyl group, an n-hexyl group, an n-decyl group, etc.; an aryl group such as a phenyl group, a 1-naphthyl group, a 2-naphthyl group, etc.; an aralkyl group such as a benzyl group, etc. The halogen-containing hydrocarbon group having from 1 to 20 carbon atoms may be derived from the hydrocarbon group as above by substituting at least one hydrogen atom therein with a suitable halogen atom, including, for example, a trifluoromethyl group. The silicon-containing group includes, for example, a trimethylsilyl group, a dimethyl(t-butyl)silyl group, etc.; the oxygen-containing group includes a methoxy group, an ethoxy group, etc.; the sulfur-containing group includes a thiol group, a sulfonic acid group, etc.; the nitrogen-containing group includes a dimethylamino group, etc.; and the phosphorus-containing group includes a phenylphosphine group, etc. $R^{10}$ and $R^{11}$, as well as $R^{15}$ and $R^{16}$ may be bonded to each other to form a ring of, for example, fluorene, etc. As specific examples of $R^{10}$ and $R^{11}$, and $R^{15}$ and $R^{16}$ of that type, mentioned are the groups of $R^8$ to $R^{18}$ except hydrogen atom. For $R^{11}$ and $R^{16}$, preferred are a hydrogen atom and an alkyl group having at most 6 carbon atoms; more preferred are a hydrogen atom, a methyl group, an ethyl group, an isopropyl group, and a cyclohexyl group; and even more preferred is a hydrogen atom. For $R^{10}$, $R^{13}$, $R^{15}$ and $R^{18}$, preferred is an alkyl group having up to 6 carbon atoms; more preferred are a methyl group, an ethyl group, an isopropyl group, and a cyclohexyl group; and even more preferred is an isopropyl group. For $R^{11}$, $R^{12}$, $R^{14}$, $R^{16}$ and $R^{17}$, preferred is a hydrogen atom. For $X^3$ and $X^4$, preferred are a halogen atom, a methyl group, an ethyl group, and a propyl group.

Specific examples of $Y^1$ include methylene, ethylene, ethylidene, isopropylidene, cyclohexylidene, 1,2-cyclohexylene, dimethylsilylene, tetramethyldisilylene, dimethylgermylene, methylborylidene ($CH_3$—B=), methylalumilidene ($CH_3$—Al=), phenylphosphylidene (Ph—P=), phenylphospholidene (PhPO=), 1,2-phenylene, vinylene (—CH=CH—), vinylidene ($CH_2$=C=), methylimido, oxygen (—O—), sulfur (—S—), etc. Of those, preferred are methylene, ethylene, ethylidene and isopropylidene, as giving better results.

$M^1$ represents titanium, zirconium or hafnium, and is preferably hafnium.

Specific examples of the transition metal compounds of formula (II) are 1,2-ethanediyl(1-(4,7-diisopropylindenyl))(2-(4,7-diisopropylindenyl))hafnium dichloride, 1,2-ethanediyl(9-fluorenyl)(2-(4,7-diisopropylindenyl))hafnium dichloride, isopropylidene(1-(4,7-diisopropylindenyl))(2-(4,7-diisopropylindenyl))hafnium dichloride, 1,2-ethanediyl(1-(4,7-dimethylindenyl))(2-(4,7-diisopropylindenyl))hafnium dichloride, 1,2-ethanediyl(9-fluorenyl)(2-(4,7-dimethylindenyl))hafnium dichloride, isopropylidene(1-(4,7-dimethylindenyl))(2-(4,7-diisopropylindenyl))hafnium dichloride, etc.; and those derived from the hafnium compounds by substituting hafnium therein with zirconium or titanium. However, the compounds are not limited to these examples.

The transition metal compounds of formula (II) can be produced, for example, according to the method described in the applicant's own prior Japanese Patent Application No. 9 296612/1997.

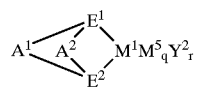
(III)

wherein $M^1$ represents titanium, zirconium or hafnium; $E^1$ and $E^2$ each represent a ligand selected from a cyclopentadienyl group, a substituted cyclopentadienyl group, an indenyl group, a substituted indenyl group, a heterocyclopentadienyl group, a substituted heterocyclopentadienyl group, an amido group, aphosphido group, a hydrocarbon group and a silicon-containing group, and they form a crosslinked structure via $A^1$ and $A^2$, and they may be the same or different; $X^5$ represents a σ-bonding ligand, and plural $X^5$'s, if any, may be the same or different, and may be crosslinked with any of other $X^5$, $E^1$, $E^2$ or $Y^2$; $Y^2$ represents a Lewis base, and plural $Y^2$'s, if any, may be the same or different, and may be crosslinked with any of other $Y^2$, $E^1$, E2 or $X^5$; $A^1$ and $A^2$ each are a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, $—SO_2—$, $—NR^7—$, $—PR^7—$, $—P(O)R^7—$, $—BR^7—$ or $—AlR^7—$, and they may be the same or different; $R^7$ represents a hydrogen atom, a halogen atom, a hydrocarbon group having from 1 to 20 carbon atoms, or a halogen-containing hydrocarbon group having from 1 to 20 carbon atoms; q represents an integer of from 1 to 5, equaling to [(atomic valency of $M^1$)—2]; and r represents an integer of from 0 to 3.

In the transition metal compounds of formula (III) (these will be hereinafter referred to as double-crosslinked complexes), $M^1$ represents titanium, zirconium or hafnium, but is preferably zirconium or hafnium. As so mentioned hereinabove, $E^1$ and $E^2$ each represent a ligand selected from a cyclopentadienyl group, a substituted cyclopentadienyl group, an indenyl group, a substituted indenyl group, a heterocyclopentadienyl group, a substituted heterocyclopentadienyl group, an amido group. (—N<), a phosphido group (—P<), a hydrocarbon group [>CR—, >C<] and a silicon-containing group [>SiR—, >Si<] (in which R indicates a hydrogen atom, a hydrocarbon group having from 1 to 20 carbon atoms, or a hetero atom-containing group), and they form a crosslinked structure via $A^1$ and $A^2$. $E^1$ and $E^2$ may be the same or different. For $E^1$ and $E^2$, preferred are a cyclopentadienyl group, a substituted cyclopentadienyl group, an indenyl group and a substituted indenyl group.

Specific examples of the σ-bonding ligand for $X^5$ include a halogen atom, a hydrocarbon group having from 1 to 20 carbon atoms, an alkoxy group having from 1 to 20 carbon atoms, an aryloxy group having from 6 to 20 carbon atoms, an amido group having from 1 to 20 carbon atoms, a silicon-containing group having from 1 to 20 carbon atoms, a phosphido group having from 1 to 20 carbon atoms, a sulfido group having from 1 to 20 carbon atoms, an acyl group having from 1 to 20 carbon atoms, etc. Plural $X^5$'s, if any, may be the same or different, and may be crosslinked with any of other $X^5$, $E^1$, $E^2$ or $Y^2$.

Specific examples of the Lewis base for $Y^2$ include amines, ethers, phosphines, thioethers, etc. Plural $Y^2$'s, if any, may be the same or different, and may be crosslinked with any of other $Y^2$, $E^1$, $E^2$ or $X^5$.

At least one crosslinking group of $A^1$ and $A^2$ is preferably a crosslinking hydrocarbon group having at least 1 carbon atom. The crosslinking group of that type includes, for example, groups of a general formula:

wherein $R^{23}$ and $R^{24}$ each represent a hydrogen atom, or a hydrocarbon group having from 1 to 20 carbon atoms, and these may be the same or different, or may be bonded to each other to form a cyclic structure; and e represents an integer of from 1 to 4. Specific examples of the group are a methylene group, an ethylene group, an ethylidene group, a propylidene group, an isopropylidene group, a cyclohexylidene group, a 1,2-cylcohexylene group, a vinylidene group ($CH_2$=C=), etc. Of those, preferred are a methylene group, an ethylene group and an isopropylidene group. $A^1$ and $A^2$ may be the same or different.

In the transition metal compounds of formula (III) where $E^1$ and $E^2$ each represent a cyclopentadienyl group, a substituted cyclopentadienyl group, an indenyl group or a substituted indenyl group, the bonding mode of the crosslinking groups of $A^1$ and $A^2$ may be of any type of double-crosslinking (1,1')(2,2') or double-crosslinking (1,2')(2,1'). Of the transition metal compounds of formula (III), preferred are those having a double-crosslinked biscyclopentadienyl derivative as the ligand and represented by the following general formula (III-a):

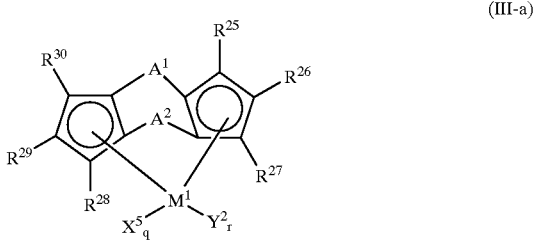

(III-a)

In formula (III-a), $M^1$, $A^1$, $A^2$, q and r have the same meanings as above. $X^5$ represents a σ-bonding ligand, and plural $X^5$'s, if any, may be the same or different, and may be bonded to any of other $X^5$ or $Y^2$ For specific examples of $X^5$, referred to are the same as those mentioned hereinabove for $X^5$ in formula (III). $Y^2$ represents a Lewis base. Plural $Y^2$'s, if any, may be the same or different, and may be bonded to any of other $Y^2$ or $X^5$. For specific examples of $Y^2$, referred to are the same as those mentioned hereinabove for $Y^2$ in formula (III). $R^{25}$ to $R^{30}$ each represent ahydrogen atom, a halogen atom, a hydrocarbon group having from 1 to 20 carbon atoms, a halogen-containing hydrocarbon group having from 1 to 20 carbon atoms, a silicon-containing group, or a hetero atom-containing group, but at least one of them must not be a hydrogen atom. $R^{25}$ to $R^{30}$ may be the same or different, and their neighboring groups may be bonded to each other to form a ring.

In the transition metal compounds having such a double-crosslinked biscyclopentadienyl derivative as the ligand, the ligand may be any of a (1,1')(2,2') double-crosslinked one or a (1,2')(2,1') double-crosslinked one.

Specific examples of the transition metal compounds of formula (III) include (1,1'-ethylene)(2,2'-ethylene)-bis(indenyl)zirconium dichloride, (1,2'-ethylene)(2,1'-ethylene)-bis(indenyl)zirconium dichloride, (1,1'-methylene)(2,2'-methylene)-bis(indenyl)zirconium dichloride, (1,2'-methylene)(2,1'-methylene)-bis(indenyl)zirconium dichloride, (1,1'-isopropylidene)(2,2'-isopropylidene)-bis(indenyl)zirconium dichloride, (1,2'-isopropylidene)(2,1'-isopropylidene)-bis(indenyl)zirconium dichloride, (1,1'-ethylene)(2,2'-ethylene)-bis(3-methylindenyl)zirconium dichloride, (1,2'-ethylene)(2,1'-ethylene)-bis(3-methylindenyl)zirconium dichloride, (1,1'-ethylene)(2,2'-ethylene)-bis(4,5-benzoindenyl)zirconium dichloride, (1,2'-ethylene)(2,1'-ethylene)-bis(4,5-benzoindenyl)zirconium dichloride, (1,1'-ethylene)(2,2'-ethylene)bis(4-isopropylindenyl)zirconium dichloride, (1,2'-ethylene)(2,1'-ethylene)-bis(4-isopropylindenyl)zirconium dichloride, (1,1'-ethylene)(2,2'-ethylene)-bis(5,6-dimethylindenyl)zirconium dichloride, (1,2'-ethylene)(2,1'-ethylene)-bis(5,6-dimethylindenyl)zirconium dichloride, (1,1'-ethylene)(2,2'-ethylene)-bis(4,7-diisopropylindenyl)zirconium dichloride, (1,2'-ethylene)(2,1'-ethylene)-bis(4,7-diisopropylindenyl)zirconium dichloride, (1,1'-ethylene)(2,2'-ethylene)-bis(4-phenylindenyl)zirconium dichloride, (1,2'-ethylene)(2,1'-ethylene)-bis(4-phenylindenyl)zirconium dichloride, (1,1'-ethylene)(2,2'-ethylene)-bis(3-methyl-4-isopropylindenyl)zirconium dichloride, (1,2'-ethylene)(2,1'-ethylene)-bis(3-methyl-4-isopropylindenyl)zirconium dichloride, (1,1'-ethylene)(2,2'-ethylene)-bis(5,6-benzoindenyl)zirconium dichloride, (1,2'-ethylene)(2,1'-ethylene)-bis(5,6-benzoindenyl)zirconium dichloride, (1,1'-ethylene)(2,2'-isopropylidene)-bis(indenyl)zirconium dichloride, (1,2'-ethylene)(2,1'-isopropylidene)-bis(indenyl) zirconium dichloride, (1,1'-isopropylidene)(2,2'-ethylene)-bis(indenyl)zirconium dichloride, (1,2'-methylene)(2,1'-ethylene)-bis(indenyl)zirconium dichloride, (1,1'-methylene) (2,2'-ethylene)-bis (indenyl)zirconium dichloride, (1,1'-ethylene)(2,2'-methylene)-bis(indenyl) zirconium dichloride, (1,1'-methylene)(2,2'-isopropylidene)-bis(indenyl)zirconium dichloride, (1,2'-methylene)(2,1'-isopropylidene)-bis(indenyl)zirconium dichloride, (1,1'-isopropylidene)(2,2'-methylene)-bis (indenyl)zirconium dichloride, (1,1'-methylene)(2,2'-methylene)(3-methylcyclopentadienyl)(cyclopentadienyl) zirconium dichloride, (1,1'-isopropylidene)(2,2'-isopropylidene)(3-methylcyclopentadienyl) (cyclopentadienyl)zirconium dichloride, (1,1'-propylidene) (2,2'-propylidene)(3-methylcyclopentadienyl) (cyclopentadienyl)zirconium dichloride, (1,1'-ethylene)(2, 2'-methylene)-bis(3-methylcyclopentadienyl)zirconium dichloride, (1,1'-methylene)(2,2'-ethylene)-bis(3-methylcyclopentadienyl)zirconium dichloride, (1,1'-isopropylidene)(2,2'-ethylene)-bis(3-methylcyclopentadienyl)zirconium dichloride, (1,1'-ethylene)(2,2'-isopropylidene)-bis(3-methylcyclopentadienyl)zirconium dichloride, (1,1'-methylene)(2,2'-methylene)-bis(3-methylcyclopentadienyl) zirconium dichloride, (1,1'-methylene)(2,2'-isopropylidene)-bis(3-methylcyclopentadienyl)zirconium dichloride, (1,1'-isopropylidene)(2,2'-isopropylidene)-bis(3-methylcylopentadienyl)zirconium dichloride, (1,1'-ethylene)(2,2'-methylene)-bis(3,4-dimethylcyclopentadienyl)zirconium dichloride, (1,1'-ethylene)(2,2'-isopropylidene)-bis(3,4-dimethylcyclopentadienyl)zirconium dichloride, (1,1'-methylene)(2,2'-methylene)-bis(3,4-dimethylcyclopentadienyl)zirconium dichloride, (1,1'-methylene)(2,2'-isopropylidene)-bis(3,4-dimethylcyclopentadienyl)zirconium dichloride, (1,1'-isopropylidene)(2,2'-isopropylidene)-bis(3,4-dimethylcyclopentadienyl)zirconium dichloride, (1,2'-ethylene)(2,1'-methylene)-bis(3-methylcyclopentadienyl) zirconium dichloride, (1,2'-ethylene)(2,1'-isopropylidene)-bis(3-methylcyclopentadienyl)zirconium dichloride, (1,2'-methylene)(2,1'-methylene)-bis(3-methylcyclopentadienyl) zirconium dichloride, (1,2'-methylene)(2,1'-isopropylidene)-bis(3-methylcyclopentadienyl)zirconium dichloride, (1,2'-isopropylidene)(2,1'-isopropylidene)-bis(3-methylcyclopentadienyl)zirconium dichloride, (1,2'-ethylene)(2,1'-methylene)-bis(3,4-dimethylcyclopentadienyl)zirconium dichloride, (1,2'-ethylene)(2,1'-isopropylidene)-bis(3,4-dimethylcyclopentadienyl)zirconium dichloride, (1,2'-methylene)(2,1'-methylene)-bis(3,4-dimethylcyclopentadienyl)zirconium dichloride, (1,2'-methylene)(2,1'-isopropylidene)-bis(3,4-dimethylcyclopentadienyl)zirconium dichloride, (1,2'-isopropylidene)(2,1'-isopropylidene)-bis(3,4-dimethylcyclopentadienyl) zirconium dichloride, etc.; and derivatives of those compounds having titanium or hafnium in place of zirconium. Needless-to-say, the compounds are not limited to these examples.

The catalyst component for olefin polymerization of the invention may contain, as the transition metal compound, one or more of the above-mentioned compounds (I) (BASF complex or Hoechst complex), (II) (single-crosslinked complex) and (III) (double-crosslinked complex) either singly or as combined.

Contacting the carrier for olefin polymerization catalysts and the transition metal compound of (I) to (III) may be effected in an inert atmosphere of nitrogen gas or the like or in a hydrocarbon such as pentane, hexane, heptane, toluene, xylene or the like. Contacting them with each other may be effected at temperatures at which monomers are polymerized to give polymers, or even at temperatures falling between −30° C. and the boiling point of the solvent used, but is preferably effected at temperatures falling between room temperature and the boiling point of the solvent used.

On the other hand, the transition metal compounds of Groups 8 to 10 of the Periodic Table for use herein are not also specifically defined, and various types of transition metal compounds falling within the range are employable herein. Preferred are those having a diimine compound as the ligand. They include, for example, complex compounds of a general formula (VII):

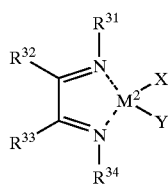
(VII)

wherein $R^{31}$ and $R^{34}$ each independently represent an aliphatic hydrocarbon group having from 1 to 20 carbon atoms, or an aromatic group having a hydrocarbon group on the ring and having up from 7 to 20 carbon atoms in total; $R^{32}$ and $R^{33}$ each independently represent a hydrogen atom, or a hydrocarbon group having from by 1 to 20 carbon atoms, and $R^{32}$ and $R^{33}$ may be bonded to each other to form a ring; X and Y each independently represent a hydrogen atom, or a hydrocarbon group having from 1 to 20 carbon atoms; and $M^2$ represents a transition metal of Groups 8 to 10 of the Periodic Table.

In formula (VII), the aliphatic hydrocarbon group having from 1 to 20 carbon atoms for $R^{31}$ and $R^{34}$ may be a linear or branched alkyl group having from 1 to 20 carbon atoms or a cycloalkyl group having from 3 to 20 carbon atoms, concretely including a methyl group, an ethyl group, an n-propyl group, an isopropyl group, an n-butyl group, an isobutyl group, a sec-butyl group, a tert-butyl group, a pentyl group, a hexyl group, an octyl group, a decyl group, a tetradecyl group, a hexadecyl group, an octadecyl group, a cyclopentyl group, a cyclohexyl group, and a cyclooctyl group, etc. Into the ring of the cycloalkyl group, a suitable substituent such as a lower alkyl group may be introduced. The aromatic group having a hydrocarbon group on the ring and having from 7 to 20 carbon atoms in total includes, for example, phenyl and naphthyl groups with at least one linear, branched or cyclic C1–10 alkyl group being on the aromatic ring. For $R^{31}$ and $R^{34}$, preferred is an aromatic group having a hydrocarbon group on the ring, and especially preferred is a 2,6-diisopropylphenyl group. $R^{31}$ and $R^{34}$ may be the same or different.

The hydrocarbon group having from 1 to 20 carbon atoms for $R^{32}$ and $R^{33}$ includes, for example, a linear or branched alkyl group having from 1 to 20 carbon atoms, a cycloalkyl group having from 3 to 20 carbon atoms, an aryl group having from 6 to 20 carbon atoms, and an aralkyl group having from 7 to 20 carbon atoms. For examples of the linear or branched alkyl group having from 1 to 20 carbon atoms and the cycloalkyl group having from 3 to 20 carbon atoms for $R^{32}$ and $R^{33}$, referred to are those of the C1–20 aliphatic hydrocarbon group mentioned hereinabove for $R^{31}$ and $R^{34}$. The aryl group having from 6 to 20 carbon atoms includes, for example, a phenyl group, a tolyl group, a xylyl group, a naphthyl group, a methylnaphthyl group, etc.; and the aralkyl group having from 7 to 20 carbon atoms includes, for example, a benzyl group, a phenethyl group, etc. $R^{31}$ and $R^{34}$ may be the same or different, and may be bonded to each other to form a ring.

For examples of the hydrocarbon group having from 1 to 20 carbon atoms for X and Y, referred to are those of the C1–20 hydrocarbon group mentioned hereinabove for $R^{32}$ and $R^{33}$. For X and Y, preferred is a methyl group. X and Y may be the same or different.

The transition metal of Groups 8 to 10 of the Periodic Table for $M^2$ includes, for example, nickel, palladium, platinum, iron, cobalt, rhodium, ruthenium, etc. Preferred are nickel and palladium.

Specific examples of the complex compounds of formula (VII) are compounds of the following formulae [1], [21], [3], [4], [5], [6], [7], [8], [9], [10], [11] and [12], etc.

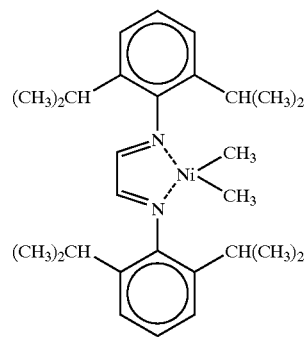
[1]

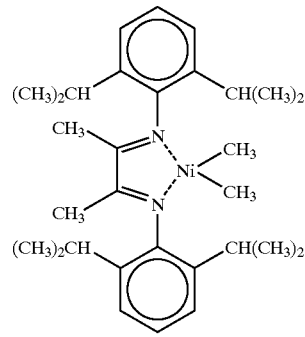
[2]

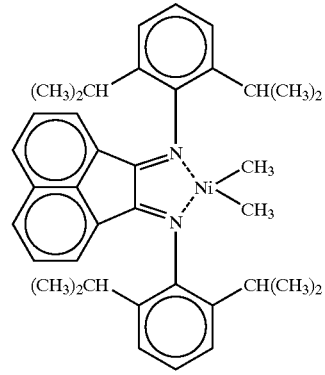
[3]

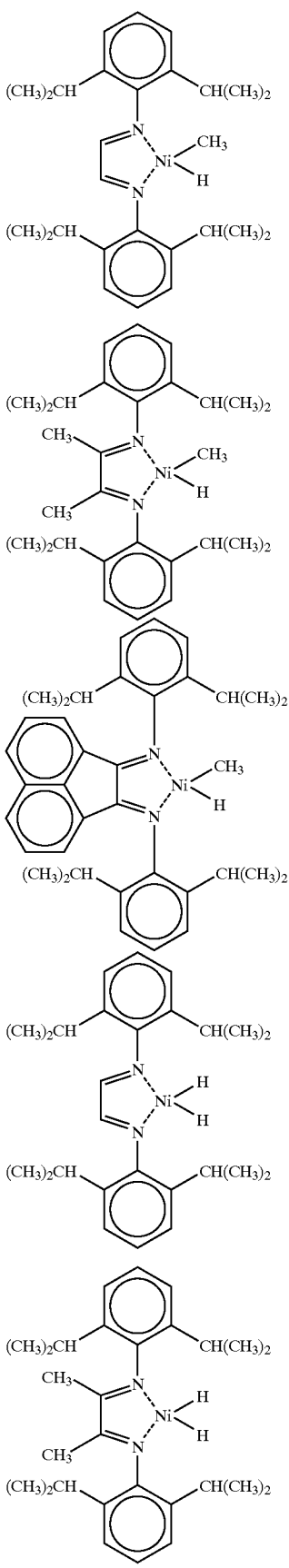
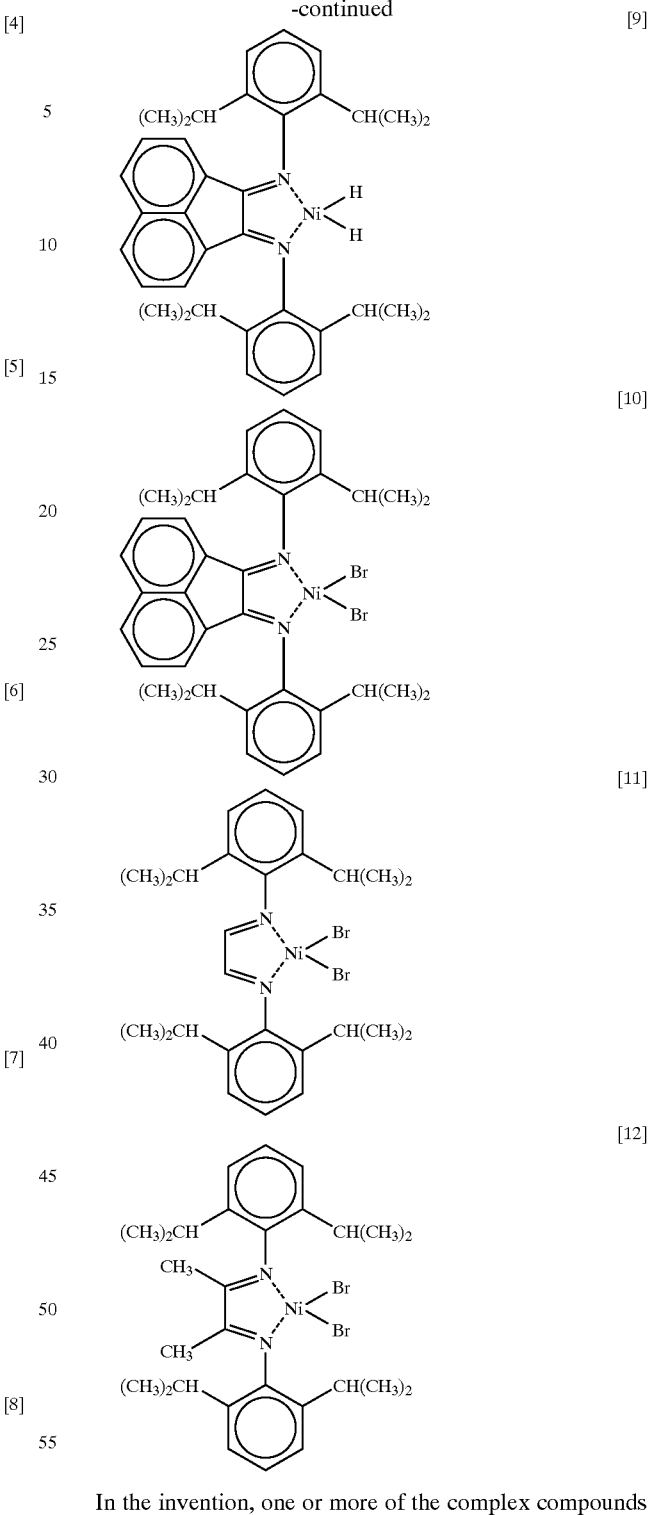

In the invention, one or more of the complex compounds noted above may be used either singly or as combined.

Contacting the carrier for olefin polymerization catalysts and the complex compound may be effected in an inert atmosphere of nitrogen gas or the like or in a hydrocarbon such as pentane, hexane, heptane, toluene, xylene or the like. Contacting them with each other maybe effected at temperatures at which monomers are polymerized to give polymers, or even at temperatures falling between −30° C. and the boiling point of the solvent used, but is preferably effected at temperatures falling between room temperature and the boiling point of the solvent used.

In the invention, if desired, the carrier for olefin polymerization catalysts and the complex compound may be ultrasonically contacted with each other to give the catalyst component for olefin polymerization. Ultrasonic waves used could improve the efficiency in contacting the carrier and the transition metal compound, whereby the catalyst produced could have much more improved activity. This will be because the reaction between the transition metal compound and the carrier could be effected in the deeper area owing to the action of the ultrasonic waves used. The mode of applying ultrasonic waves to the components is not specifically defined. For example, they may be applied to either the carrier or the complex compound, or to both the two, the carrier and the complex compound. Ultrasonic waves may be applied thereto twice or more in the series of the reaction. The output of the ultrasonic waves to be employed may fall between 1 and 1000 kHz, but preferably between 10 and 500 kHz.

4. Method of Producing Polyolefins:

The method of using the polymerization catalyst along with an organoaluminum compound for polyolefin production of the invention is favorable to homopolymerization of olefins and also to copolymerization of olefins with other olefins and/or other monomers (that is, copolymerization of different types of olefins, or copolymerization of olefins with other monomers, or copolymerization of different types of olefins with other monomers).

The organoaluminum compound includes, for example, linear aluminoxanes of formula (IV), cyclic aluminoxanes of formula (V) and alkyl group-having aluminum compounds of formula (VI).

Concretely, it includes trialkylaluminum compounds such as trimethylaluminum, triethylaluminum, tripropylaluminum, triisobutylaluminum, tri-n butylmethylaluminum, triisobutylaluminum, tri-sec-butylmethylaluminum, tri-tert-butylmethylaluminum, tripentylaluminum, trihexylaluminum, trioctylaluminum, tridecylaluminum, tricyclohexylaluminum, tricyclooctylaluminum, etc.; halogen-, alkoxy group- or hydroxyl group-having alkylaluminum compounds such as dimethylaluminum chloride, diethylaluminum chloride, ethylaluminum sesquichloride, dimethylaluminum methoxide, diethylaluminum methoxide, dimethylaluminum hydroxide, diethylaluminum hydroxide, etc.; hydrogen atom-having aluminum compounds such as dimethylaluminum hydride, diisobutylaluminum hydride; aluminoxanes such as methylaluminoxane, ethylaluminoxane, isobutylaluminoxane, etc. Of those, preferred are trialkylaluminum compounds, and more preferred is triisobutylaluminum.

In the invention, one or more of those organoaluminum compounds noted above may be used either singly or as combined.

The olefins are not specifically defined, but preferred are α-olefins having from 2 to 20 carbon atoms. The α-olefins include, for example, α-olefins such as ethylene, propylene, 1-butene, 3-methyl-1-butene, 4-methyl-1-butene, 4-phenyl-1-butene, 1-pentene, 3-methyl-1-pentene, 4-methyl-1-pentene, 3,3-dimethyl-1-pentene, 3,4-dimethyl-1-pentene, 4,4-dimethyl-1-pentene, 1-hexene, 4-methyl-1-hexene, 5-methyl-1-hexene, 6-phenyl-1-hexene, 1-octene, 1-decene, 1-dodecene, 1-tetradecene, 1-hexadecene, 1-octadecene, 1-eicosene, vinylcyclohexane, etc.; halogen-substituted α-olefins such as hexafluoropropene, tetrafluoroethylene, 2-fluoropropene, fluoroethylene, 1,1-difluoroethylene, 3-fluoropropene, trifluoroethylene, 3,4-dichloro-1-butene, etc.; cyclic olefins such as cyclopentene, cyclohexene, norbornene, 5-methylnorbornene, 5-ethylnorbornene, 5-propylnorbornene, 5,6-dimethylnorbornene, 5-benzylnorbornene, etc. Styrenic compounds are also usable as olefins herein. They include, for example, styrene; alkylstyrenes such as p-methylstyrene, p-ethyistyrene, p-propylstyrene, p-isopropylstyrene, p-butylstyrene, p-tert-butylstyrene, p-phenylstyrene, o-methylstyrene, o-ethylstyrene, o-propylstyrene, o-isopropylstyrene, m-methylstyrene, m-ethylstyrene, m-isopropylstyrene, m-butylstyrene, mesitylstyrene, 2,4-dimethylstyrene, 2,5-dimethylstyrene, 3,5-dimethylstyrene, etc.; alkoxystyrenes such as p-methoxystyrene, o-methoxystyrene, m-methoxystyrene, etc.; halogenostyrenes such as p-chlorostyrene, m-chlorostyrene, o-chlorostyrene, p-bromostyrene, m-bromostyrene, o-bromostyrene, p-fluorostyrene, m-fluorostyrene, o-fluorostyrene, o-methyl-p-fluorostyrene, m-fluorostyrene, o-fluorostyrene, o-methyl-p-fluorostyrene, etc.; and also trimethylsilylstyrene, vinylbenzoates, divinylbenzene, etc. The other olefins to be copolymerized may be suitably selected from the olefins noted above.

In the invention, one or more olefins may be homopolymerized or copolymerized either singly or as combined. Where two or more different olefins are copolymerized, the olefins noted above may be combined in any desired manner.

In the invention, olefins such as those mentioned above may be copolymerized with any other comonomers. The comonomers include, for example, linear diolefins such as butadiene, isoprene, 1,4-pentadiene, 1,5-hexadiene, etc.; polycyclic olefins such as norbornene, 1,4,5,8-dimethano-1,2,3,4,4a,5,8,8a-octahydronaphthalene, 2-norbornene, etc.; cyclic diolefins such as norbornadiene, 5-ethylidenenorbornene, 5-vinylnorbornene, dicyclopentadiene, etc.; and unsaturated esters such as ethyl acrylate, methyl methacrylate, etc.

The mode of olefin polymerization is not specifically defined, and herein employable is any desired polymerization mode of slurry polymerization, solution polymerization, vapor-phase polymerization, bulk polymerization, suspension polymerization or the like.

Solvents may be used in polymerization. They include, for example, hydrocarbons and halogenohydrocarbons such as benzene, toluene, xylene, n-hexane, n-heptane, cyclohexane, chloromethylene, chloroform, 1,2-dichloroethane, chlorobenzene, etc. One or more such solvents may be used either singly or as combined. Depending on their type, monomers to be polymerized may also serve as solvents.

In view of the catalytic activity for polymerization and of the reactor efficiency, it is desirable that the amount of the catalyst to be in the polymerization system is so controlled that the transition metal catalyst component could fall generally between 2 and 100 ∥mols, but preferably between 7 and 25 μmols, in one liter of the solvent in the system.

Regarding the polymerization condition, the pressure may fall generally between ordinary pressure and 2000 kg/cm$^2$G. The reaction temperature may fall generally between −50 and 250° C. For controlling the molecular weight of the polymers to be produced, the type and the amount of the catalyst components to be used and the polymerization temperature will be suitably selected. If desired, hydrogen may be introduced into the polymerization system for that purpose.

The invention is described in more detail with reference to the following Examples and Comparative Examples, which, however, are not intended to restrict the scope of the invention.

EXAMPLE 1

(1) Preparation of Aluminum-oxy Compound:

Methylalumoxane was used as the starting aluminum-oxy compound. 1.0 liter of a solution of methylalumoxane in toluene was prepared (having a concentration of 1.5 mols/liter, and containing 14.5% by weight of trimethylaluminum from Albemarle) was prepared. The solvent was evaporated away from this under a reduced pressure (10 mmHg) at 60° C. to give a dry solid. In this condition, the dry solid was left for 4 hours, and then cooled to room temperature. Thus was obtained dried-up methylaluminoxane. This was again dissolved in dewatered toluene so that its volume could be the same as the original volume having contained the solvent. The resulting solution was subjected to $^1$H-NMR to measure the trimethylaluminum content of methylaluminoxane, and the content was 3.6% by weight. On the other hand, the total aluminum content of the solution was measured through fluorescent X-ray analysis (ICP), and was 1.32 mols/liter. Next, the solution was left static for full 2 days, and the insoluble component was allowed to settle out. Next, the resulting supernatant was filtered through a G5 glass filter in a nitrogen atmosphere, and the filtrate of the supernatant was recovered. Thus was obtained methylalumoxane (a) of the intended aluminum-oxy compound. Through ICP, this was found to have a concentration of 1.06. In the process, 10.9% by weight of organoaluminum and 17.3% by weight of the insoluble component were removed from the product.

(2) Preparation of Carrier for Olefin Polymerization Catalysts:

27.1 g of $SiO_2$ (P-10 from Fuji Silicia Chemical) was dried under reduced pressure at 200° C. for 4.0 hours in a minor nitrogen stream to obtain 25.9 g of dry $SiO_2$. The dry $SiO_2$ was put into 400 ml of dewatered toluene (this was previously cooled to −78° C. in a dry ice/methanol bath), and stirred. With stirring, 145.5 ml of the toluene solution of methylalumoxane (a) prepared in above (1) was dropwise added to the resulting toluene suspension of $SiO_2$, via a dropping funnel, and the time taken until the complete addition was 2 hours.

Next, this was stirred for 4.0 hours, then heated from −78° C. up to 20° C. over a period of 6.0 hours, and thereafter left as such for 4.0 hours. Next, this was further heated from 20° C. up to 80° C. over a period of 1 hour, and left at 80° C. for 4.0 hours whereby the reaction between silica and methylaluminoxane was completed. The resulting suspension was filtered at 80° C., and the solid thus obtained was washed twice with 400 ml of dewatered toluene at 60° C. and then twice with 400 ml of dewatered n-heptane at 60° C. The thus-washed solid was dried under reduced pressure at 60° C. for 4.0 hours to obtain 33.69 g of methylaluminoxane-carrying $SiO_2$, which serves as a carrier for olefin polymerization catalysts. The on-carrier ratio of methylaluminoxane was 30.1% per gram of $SiO_2$.

Dewatered n-heptane was added to the whole of the thus-obtained, methylaluminoxane-carrying $SiO_2$ to make a total volume of 500 ml. The resulting suspension had a methylaluminoxane concentration of 0.27 mols/liter.

(3) Preparation of Catalyst Component:

As a transition metal compound of Group 4 of the Periodic Table, herein used was rac-$Me_2Si(2$-Me-4-PhInd$)_2$ $ZrCl_2$ (chemical name: dimethylsilanediyl-bis-1-(2-methyl-4-phenylindenyl)zirconium dichloride). 2.0 mmols (7.41 ml) of the methylaluminoxane-carrying $SiO_2$ prepared in above (2) was put into a 50-ml container having been purged with nitrogen, to which was added 20 ml of dewatered toluene, and stirred. To the resulting suspension, added was 0.2 ml (2.0 μmols) of a toluene solution of rac-$Me_2Si$ (2-Me-4-PhInd$)_2ZrCl_2$ (10 μmols/ml), and further stirred at room temperature for 0.5 hours. Next, stirring was stopped, and the solid catalyst component was allowed to settle out. It was confirmed that the settled solid catalyst component was red and the supernatant solution was colorless and transparent. The solution was removed through decantation, and 20 ml of n-heptane was added to the residue. Thus was obtained an $SiO_2$-carried metallocene catalyst slurry.

(4) Polymerization of Propylene:

A 1.4-liter, stainless, pressure autoclave equipped with a stirrer was heated at 80° C., and then fully dried under reduced pressure. This was restored to have an atmospheric pressure with dry nitrogen, and cooled to room temperature. Next, 400 ml of dry, oxygen-free n-heptane and 0.7 mmols of triisobutylaluminium (in toluene) were put into the autoclave in a dry nitrogen atmosphere, and stirred at 500 rpm. After having been heated up to 50° C. over a period of 5 minutes, this was further stirred for 5 minutes. To this was added the $SiO_2$-carried metallocene catalyst prepared in above (3), and heated up to 60° C. In that condition, propylene was continuously introduced into the autoclave under a gauge pressure of 7.0 kg/cm$^2$, and polymerized therein for 1.5 hours.

After the reaction, the catalyst was deactivated with a small amount of methanol, and the non-reacted propylene was removed by degassing the autoclave. The reaction mixture was put into a large amount of methanol and washed with it, and thereafter filtered and dried. As a result, 182.8 g of polypropylene was obtained. The catalyst activity was 668.1 (kg/g-Zr·hr), and the bulk density of the polymer obtained was 0.39 (g/cc).

EXAMPLE 2

The same process as in Example 1 was repeated, except that $SiO_2$ was dried at 150° C. but not at 200° C. in the step (2) of preparing the carrier for olefin polymerization catalysts. As a result, the on-carrier ratio of methylaluminoxane of the carrier obtained herein was 70.0% per gram of $SiO_2$. The amount of polypropylene produced herein was 179.0 g. The catalyst activity was 654.2 (kg/g-Zr·hr), and the bulk density of the polymer was 0.38 (g/cc).

EXAMPLE 3

The same process as in Example 1 was repeated. In this, however, the compound of formula [11] (4.0 μmols) (this is a transition metal compound of Groups 8 to 10 of the Periodic Table) was used in the step (3), in place of the transition metal compound of Group 4 of the Periodic Table, rac-$Me_2Si(2$-Me-4-PhInd$)_2ZrCl_2$ (2.0 μmols) used in Example 1. Thus was obtained an $SiO_2$-carried metallocene catalyst slurry (b).

A 1.4-liter, stainless, pressure autoclave equipped with a stirrer was heated at 80° C., and then fully dried under reduced pressure. This was restored to have an atmospheric pressure with dry nitrogen, and cooled to room temperature. Next, 400 ml of dry, oxygen-free toluene and 0.7 mmols of triisobutylaluminium (in toluene) were put into the autoclave in a dry nitrogen atmosphere, and stirred at 500 rpm. After having been heated up to 30° C. over a period of 5 minutes, this was further stirred for 5 minutes.

To this was added the catalyst (b), and heated up to 40° C. In that condition, ethylene was continuously introduced into the autoclave under a gauge pressure of 7.0 kg/cm$^2$, and polymerized therein for 1 hour.

After the reaction, the catalyst was deactivated with a small amount of methanol, and the non-reacted ethylene was removed by degassing the autoclave. The reaction mixture was put into a large amount of methanol and washed with it, and thereafter filtered and dried. As a result, 21.3 g of polyethylene was obtained. The catalyst activity was 90.7 (kg/g-Ni·hr), and the bulk density of the polymer obtained was 0.37 (g/cc).

Comparative Example 1

The same process as in Example 1 was repeated, except that methylaluminoxane not having been subjected to the insoluble component removing treatment was used herein in place of the methylaluminoxane (a) prepared in (1) in Example 1. The on-carrier ratio of methylaluminoxane in the methylaluminoxane-carrying $SiO_2$ carrier prepared herein was 69.7% of the weight of $SiO_2$. The amount of polypropylene produced herein was 25.0 g. The catalyst activity was 91.4 (kg/g-Zr·hr). Regarding its morphology, the polymer obtained herein was not granular, but contained whiskers and aggregates. The on-carrier catalyst prepared and used herein was ineffective for realizing the intended polymer morphology.

Comparative Example 2

The same process as in Example 1 was repeated. In this, however, a toluene solution of methylaluminoxane (1.5 mols/liter, from Albemarle) was directly used without being subjected to the solvent and insoluble component removing treatment, in place of the methylaluminoxane (a) prepared in (1) in Example 1. The on-carrier ratio of methylaluminoxane in the methylalilminoxane-carrying $SiO_2$ carrier prepared herein was 7.5% of the weight of $SiO_2$. The amount of polypropylene produced herein was 19.0 g. The catalyst activity was 69.5 (kg/g-Zr·hr) . Regarding its morphology, the polymer obtained herein contained some aggregates and was not good.

Comparative Example 3

The same process as in Example 3 was repeated. In this, however, a toluene solution of methylaluminoxane (1.5 mols/liter, from Albemarle) was directly used without being subjected to the solvent and insoluble component removing treatment, in place of the methylaluminoxane (a) prepared in (1) in Example 1. The on-carrier ratio of methylaluminoxane in the methylaluminoxane-carrying $SiO_2$ carrier prepared herein was 7.5% of the weight of $SiO_2$. The amount of polyethylene produced herein was 6.2 g. The catalyst activity was 26.4 (kg/g-Zr·hr), and the bulk density of the polymer was 0.15 (g/cc).

INDUSTRIAL APPLICABILITY

The aluminum-oxy compound, the carrier for olefin ploymerization catalysts, and the catalyst component for olefin polymerzation of the invention are better than conventional transition metal compound-carrying catalysts, as being able to increase the catalyst activity to give high bulk-density polymers. These are favorable to bulk polymerization, vapor-phase polymerization, slurry polymerization, etc.

What is claimed is:

1. A carrier for olefin polymerization catalysts, which comprises:
   i) an aluminum-oxy compound prepared by reacting an organoaluminum compound with water and formulating the material obtained as a solution with a solvent, and removing the solvent from the solution thereby resulting in an aluminum-oxy compound as a dry solid that is then solubilized in a hydrocarbon solvent from which insoluble matter that separates from solution is removed thereby resulting in a solution of aluminum-oxy compound in which the amount of the organoaluminum compound remaining is at most 10% by weight as measured by $^1H$—NMR; and
   ii) an inorganic compound which is a compound of at least one element selected from the group consisting of Groups 2 to 4 and Groups 12 to 14 of the Periodic Table.

2. The carrier for olefin polymerization catalysts as claimed in claim 1, wherein the inorganic compound is an oxide.

3. A catalyst component for olefin polymerization, which comprises the carrier for olefin polymerization catalysts of claim 1 and a transition metal compound.

4. The catalyst component for olefin polymerization as claimed in claim 3, wherein the transition metal compound is selected from the group consisting of Group 4 and Groups 8 to 10 of the Periodic Table.

5. The catalyst component for olefin polymerization as claimed in claim 3, wherein the transition metal compound of Group 4 of the Periodic Table is a compound of formula (I), (II) or (III):

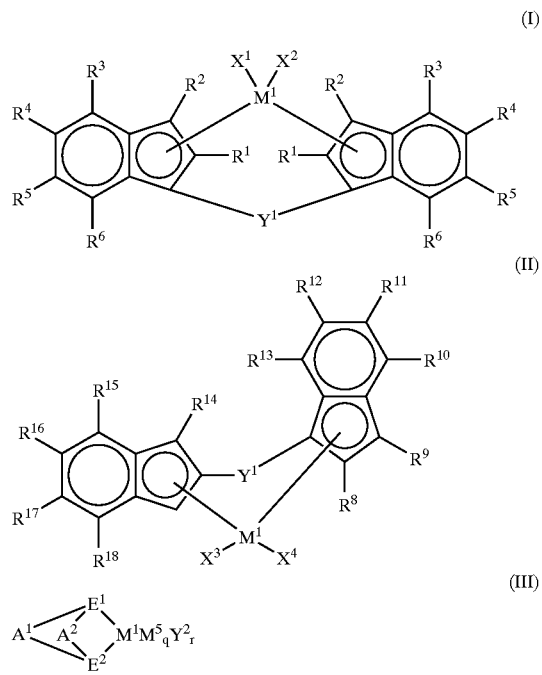

where $R^1$ to $R^6$ each independently represent a hydrogen atom, a halogen atom, a hydrocarbon group having from 1 to 20 carbon atoms, or a halogen-containing hydrocarbon group having from 1 to 20 carbon atoms; the groups of at least one pair of $R^3$ and $R^4$, $R^4$ and $R^5$, and $R^5$ and $R^6$ may be bonded to each other to form a ring; $X^1$ and $X^2$ each independently represent a hydrogen atom, a halogen atom, or a hydrocarbon group having from 1 to 20 carbon atoms; $Y^1$ is a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, —$SO_2$—, —$NR^7$—, —$PR^7$—, —$P(O)R^7$—, —$BR^7$— or —$AlR^7$—;

$R^7$ represents a hydrogen atom, a halogen atom, a hydrocarbon group having from 1 to 20 carbon atoms, or a halogen-containing hydrocarbon group having from 1 to 20 carbon atoms; $M^1$ represents titanium, zirconium or hafnium; where $R^8$ to $R^{18}$, $X^3$ and $X^4$ each independently represent a hydrogen atom, a halogen atom, a hydrocarbon group having from 1 to 20 carbon atoms, a halogen-containing hydrocarbon group having from 1 to 20 carbon atoms, a silicon-containing group, an oxygen-containing group, a sulfur-containing group, a nitrogen-containing group, or a phosphorus-containing group; $R^{10}$ and $R^{11}$, as well as $R^{15}$ and $R^{16}$ may be bonded to each other to form a ring; $X^3$ and $X^4$ each independently represent a halogen atom, a hydrocarbon group having from 1 to 20 carbon atoms, a halogen-containing hydrocarbon group having from 1 to 20 carbon atoms, a silicon-containing group, an oxygen-containing group, a sulfur-containing group, a nitrogen-containing group, or a phosphorus-containing group; $Y^1$ is a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, —SO$_2$—, —NR$^7$—, —PR$^7$—, —P(O)R$^7$—, —BR$^7$— or —AlR$^7$—; $R^7$ represents a hydrogen atom, a halogen atom, a hydrocarbon group having from 1 to 20 carbon atoms, or a halogen-containing hydrocarbon group having from 1 to 20 carbon atoms; $M^1$ represents titanium, zirconium or hafnium;

where $M^1$ represents titanium, zirconium or hafnium; $E^1$ and $E^2$ each represent a ligand selected from a cyclopentadienyl group, a substituted cyclopentadienyl group, an indenyl group, a substituted indenyl group, a heterocyclopentadienyl group, a substituted heterocyclopentadienyl group, an amido group, a phosphido group, a hydrocarbon group and a silicon-containing group, and they form a crosslinked structure via $A^1$ and $A^2$, and they may be the same or different; $X^5$ represents a σ-bonding ligand, and plural $X^5$'s, if any, may be the same or different, and may be crosslinked with any of other $X^5$, $E^1$, $E^2$ or $Y^2$; $Y^2$ represents a Lewis base, and plural $Y^2$'s, if any, may be the same or different, and may be crosslinked with any of other $Y^2$, $E^1$, $E^2$ or $X^5$; $A^1$ and $A^2$ each are a divalent crosslinking group via which the two ligands are bonded to each other, representing a hydrocarbon group having from 1 to 20 carbon atoms, a halogen-containing hydrocarbon group having from 1 to 20 carbon atoms, a silicon-containing group, a germanium-containing group, a tin-containing group, —O—, —CO—, —S—, —SO$_2$—, —NR$^7$—, —PR$^7$—, —P(O)R$^7$—, —BR$^7$— or —AlR$^7$—, and they may be the same or different; $R^7$ represents a hydrogen atom, a halogen atom, a hydrocarbon group having from 1 to 20 carbon atoms, or a halogen-containing hydrocarbon group having from 1 to 20 carbon atoms; q represents an integer of from 1 to 5, equaling to [(atomic valency of $M^1$)–2]; and r represents an integer of from 0 to 3.

6. The catalyst component for olefin polymerization as claimed in claim 4, wherein the transition metal compound of Groups 8 to 10 of the Periodic Table has a diimine compound as the ligand.

7. A catalyst component for olefin polymerization, which comprises the catalyst component for olefin polymerization of claim 4 and an organoaluminum compound.

8. A method for producing polyolefins, which comprises: polymerizing olefins in the presence of the catalyst component for olefin polymerization of claim 3.

9. The carrier for olefin polymerization catalysts as claimed in claim 1, wherein the element of Groups 2 to 4 and 12 to 14 of the inorganic compound is C, Mg, Al, Si, Ca, Sc, Ti, B, Tl, Ge, Sn, Zn, Ba, Pb, Y, Sr or Th.

10. The carrier for olefin polymerization catalysts as claimed in claim 9, wherein the inorganic compound is SiO$_2$, Al$_2$O$_3$, MgO, ZrO$_2$, TiO$_2$, Fe$_2$O$_3$, B$_2$O$_3$, CaO, ZnO, BaO, ThO$_2$ or mixtures thereof.

11. The carrier for olefin polymerization catalysts as claimed in claim 9, wherein the inorganic compound is a magnesium compound of the formula:

$$MgR^{22}_x X^6_y$$

wherein $R^{22}$ is $C_{1-20}$-alkyl, $C_{1-20}$-alkoxy or $C_{6-20}$-aryl; $X^6$ is halogen or $C_{1-20}$-alkyl; x is 0, 1 or 2; y is 0, 1 or 2 and x+y=2 and the groups of $R^{22}$ and $X^6$ individually may be the same or different.

12. The carrier for olefin polymerization catalysts as claimed in claim 9, wherein the inorganic compound has a mean grain size of 1 to 300 μm.

13. The carrier for olefin polymerization catalysts as claimed in claim 1, wherein the solvent is removed from the material by heating the material up to a temperature of 80° C. under reduced pressure.

14. The carrier for olefin polymerization catalysts as claimed in claim 13, wherein the solvent is removed from the material at a temperature up to 60° C.

15. The carrier for olefin polymerization catalysts as claimed in claim 1, wherein the amount of the organoaluminum compound remaining ranges from 3 to 5% by weight.

16. The carrier for olefin polymerization catalysts as claimed in claim 1, wherein the solvent is a member selected from the group consisting of aromatic hydrocarbons, aliphatic hydrocarbons, alicyclic hydrocarbons and petroleum fractions.

* * * * *